United States Patent [19]

Henderson et al.

[11] Patent Number: 5,219,538

[45] Date of Patent: * Jun. 15, 1993

[54] GAS AND OXYGEN CARRYING LIPID VESICLES

[75] Inventors: Sheryl L. Henderson, Weare; Donald F. H. Wallach, Hollis; Rajiv Mathur, Nashua, all of N.H.

[73] Assignee: Micro-Pak, Inc., Wilmington, Del.

[ * ] Notice: The portion of the term of this patent subsequent to Apr. 14, 2009 has been disclaimed.

[21] Appl. No.: 662,850

[22] Filed: Mar. 1, 1991

Related U.S. Application Data

[63] Continuation-in-part of Ser. No. 598,120, Oct. 16, 1990, Pat. No. 5,160,669, which is a continuation-in-part of Ser. No. 410,650, Sep. 2, 1989, Pat. No. 5,019,174, which is a continuation-in-part of Ser. No. 157,571, Mar. 3, 1988, Pat. No. 4,911,928, said Ser. No. 598,120, is a continuation-in-part of Ser. No. 443,516, Nov. 29, 1989, Pat. No. 5,147,723, which is a continuation of Ser. No. 157,571, Mar. 3, 1988, Pat. No. 4,911,928.

[51] Int. Cl.$^5$ .................... A61K 9/127; B01J 13/12
[52] U.S. Cl. .................... 428/402.2; 106/312; 264/4.1; 264/4.3; 264/4.32; 264/4.33; 264/4.6; 264/4.7; 424/450; 436/829; 514/832
[58] Field of Search .......... 264/4.1, 4.3, 4.32, 264/4.33, 4.6, 4.7; 428/402.2; 424/450; 436/829; 514/832

[56] References Cited

U.S. PATENT DOCUMENTS

| | | | |
|---|---|---|---|
| 2,980,941 | 4/1961 | Miller | 15/506 |
| 3,528,925 | 9/1970 | Chapuis | 252/559 |
| 4,212,758 | 7/1980 | Shashkina et al. | 252/119 |
| 4,217,344 | 8/1980 | Vanlerberghe et al. | 424/450 X |
| 4,297,374 | 10/1981 | Wess | 514/777 |
| 4,448,765 | 5/1984 | Ash et al. | 424/450 |
| 4,452,818 | 6/1984 | Haidt | 424/352 |
| 4,536,324 | 8/1985 | Fujiwara et al. | 252/311 |
| 4,622,219 | 11/1986 | Haynes | 424/450 |
| 4,722,904 | 2/1988 | Feil | 436/11 |
| 4,742,050 | 5/1988 | Yuhas et al. | 514/34 |
| 4,743,449 | 5/1988 | Yoshida et al. | 424/420 |
| 4,776,991 | 10/1988 | Farmer et al. | 264/4.3 |
| 4,814,270 | 3/1989 | Piran | 435/7 |
| 4,830,857 | 5/1989 | Handjani et al. | 424/450 |
| 4,865,836 | 9/1989 | Long, Jr. | 424/5 |
| 4,911,928 | 3/1990 | Wallach | 424/450 |
| 4,942,038 | 7/1990 | Wallach | 424/450 |
| 4,987,154 | 1/1991 | Long, Jr. | 514/772 |
| 4,993,415 | 2/1991 | Long | 128/653 |
| 5,061,484 | 10/1991 | Heldebrant | 424/78 |
| 5,077,036 | 12/1991 | Long, Jr. | 424/5 |
| 5,080,885 | 1/1992 | Long, Jr. | 424/5 |
| 5,088,499 | 2/1992 | Unger | 424/450 X |
| 5,104,736 | 4/1992 | Wallach | 424/450 X |

FOREIGN PATENT DOCUMENTS 0375610 6/1990 European Pat. Off. .
WO91/00110 1/1991 PCT Int'l Appl. .

Primary Examiner—Richard D. Lovering

[57] ABSTRACT

The present invention relates to the production of lipid vesicles having a moderately volatile material such as a perfluorocarbon or a silicone oil encapsulated therein. In another aspect, lipid vesicles having a gas-filled center or core are made. The lipid vesicles having gas-filled central core are made by dehydrating vesicles having the moderately volatile liquid encapsulated in the central core. This drives off the water first, allowing the moderately volatile liquid to stabilize the vesicle structure as it dries, finally forming a central void which can refract light. The preferred vesicles of the invention are paucilamellar vesicles.

19 Claims, No Drawings

GAS AND OXYGEN CARRYING LIPID VESICLES

REFERENCE TO RELATED APPLICATIONS

This application is a continuation-in-part of U.S. patent application Ser. No. 590,120, filed Oct. 16, 1990, now U.S. Pat. No. 5,160,669, entitled "Method of Making Oil Filled Paucilamellar Lipid Vesicles," which is a continuation-in-part of U.S. patent application Ser. No. 410,650, filed Sept. 2, 1989, now U.S. Pat. No. 5,019,174, entitled "Liposomal Cleaner," which is a continuation-in-part of U.S. Pat. Nos. 157,571, filed Mar. 3, 1988 and 4,911,928, entitled "Paucilamellar Lipid Vesicles." U.S. patent application Ser. No. 598,120,now U.S. Pat. No. 5,160,669, is also a continuation-in-part of U.S. patent application Ser. No. 443,516, filed Nov. 26, 1989, now U.S. Pat. No. 5,147,723, entitled "Paucilamellar Lipid Vesicles," which is a continuation of the aforementioned U.S. Pat. No. 4,911,928. The disclosures of all the above applications and patents are incorporated herein by reference.

BACKGROUND OF THE INVENTION

The present invention concerns certain special purpose lipid vesicles, specifically lipid vesicles with voids and oxygen carrying capacity. These special lipid vesicles have significant uses industrially. The vesicles with voids can be used as whiteners for the paint industry, while oxygen carrying vesicles are particularly useful in the biological sciences, e.g., as artificial oxygen suppliers. While the different aspects of the invention may appear somewhat diverse, the broad applicability of the methods described herein to both aspects of the invention shall be readily apparent from the following description.

Paucilamellar lipid vesicles, e.g., those described in U.S. Pat. No. 4,911,928, the disclosure of which is incorporated herein by reference, have 2–10 substantially spherical lipid bilayers surrounding a large, amorphous cavity or core. The lipid bilayers are hydrated, having bound water entrapped between the bilayers. The central cavity may encapsulate an aqueous solution, or a water immiscible oil or wax can fill part or all of the core.

There have been numerous attempts at drying aqueous filled lipid vesicles, primarily using a variety of lyophilization methods. In most instances, a cryoprotectant such as high molecular weight dextran or other carbohydrate has been used to preserve the lipid wall structure as the aqueous solution is removed. Without this cryoprotectant, the dehydrated bilayers collapse, forming a solid bilamellar array which is often distinguishable microscopically by visible optical bifringence. These lyophilization methods have been moderately successful, allowing rehydration (and, accordingly, reconstitution) of the lipid vesicles. The cryoprotectants are deposited around the bilayers, allowing reformation of the vesicles from the lamellar skeletons upon rehydration. However, unless rehydration is by using a vapor rather than liquid phase, there normally is some loss of encapsulated water soluble material into the external aqueous phase. The use of cryoprotectants provides a measure of stability to the spherical bilayer shells by preventing the aggregation of vesicles during dehydration. This does not prevent collapse of the vesicle core for paucilamellar lipid vesicles.

The situation is somewhat different if a nonvolatile hydrophobic material such as a paraffin wax is encapsulated in the amorphous central cavity of a paucilamellar vesicle. These vesicles have a monolayer of a surfactant surrounding the hydrophobic core, either from cannibalizing the wall material or by adding a separate, indifferent (or nonvesicle forming surfactant) in the manufacture of the vesicle. As the water is removed, the surfactant stabilized wax droplets limit the collapse of this central core, forming tiny, solid particles and leading to relatively easy rehydration.

While it is possible to make vesicles with a hydrophobic core encapsulating a liquid which is more volatile than the aqueous solution bound in the bilayers, this procedure does not lead to dry vesicles with a void in the center. These volatile materials, e.g., organic solvents, volatilize before the water as the vesicles are dried. As the drying continues, the core which had been filled by the volatile material leaches water from the bilayers into the central cavity. The vesicles shrink, forming small aqueous filled paucilamellar lipid vesicles that give up their water as if there had never been any volatile liquid in the core.

None of the described methods have provided means for forming stable, dry lipid vesicles with a void-like gaseous (or air) filled core. This particular type of vesicle would have particular applicability in the paint and cosmetic industries. The two types of whiteners which presently provide the primary whitening capacity for the paint and cosmetic industries are titanium dioxide pigments ($TiO_2$) and polymer particles with voids. Although $TiO_2$ has a long history as a whitener, the paint and cosmetic industries have been trying to move away from this type of heavy metal whitener. Rohm & Haas developed a whitener primarily for the paint industry, sold under the trademark Rhopaque TM, which is a small polymer sphere having an air space of less than 0.2 mm. This small but distinct central cavity provides optical scattering so the particle acts as a whitener. A lipid vesicle which could be dried and have a similar central cavity could provide the same whitening capacity while having the further advantages of biodegradability and cost competitiveness.

Since lipid vesicles having this type of gas-filled center cannot be made from aqueous filled vesicles, nonvolatile hydrophobic filled vesicles, or vesicles filled with highly volatile hydrophobic materials, the present invention relates to the use of moderately volatile liquids as an attempt to solve the problem. As used herein, the term "moderately volatile liquid" means and implies a liquid that is less volatile than water but more volatile than the lipids which form the bilayer structure of the vesicles. These moderately volatile liquids have a vapor pressure such that they are able to leach out of the lipid vesicles when air dried, dried under a vacuum, or lyophilized, but they do so at a slower rate than the encapsulated aqueous solution. Accordingly, substantially all of the aqueous solution encapsulated in the vesicle, as well as the aqueous solution surrounding the vesicle, evaporates before the moderately volatile liquid and the moderately volatile liquid provides structure to the vesicle as the water is removed.

Other requirements for this moderately volatile liquid included substantial immiscibility in aqueous solutions and the lipids forming the vesicles, as well as substantial unreactivity with the lipid. A class of materials which meet all these requirements are the perfluorocarbons. Perfluorocarbons are, primarily, alkanes or cycloalkanes having all of the hydrogens replaced with fluorines. Certain of these perfluorocarbons, primarily, perfluorodecalin and perfluorotripropylamine, have an additional advantage; they can function as oxygen carriers. Most perfluorocarbons have a density of about two, have a high air-and oxygen-carrying capacity, and are substantially unreactive with most materials. Encapsulation of oxygen-rich perfluorocarbons could have substantial value for use in cosmetics or in fermentation because of their high in vitro oxygenation capacity. In addition, these materials have promise for a substantial number of medical uses. For example, for these materials would be advantageous if used as an infusion after trauma, for infusion for radiotherapy, for wound perfusion, in angioplasty, or in radioimaging.

Accordingly, an object of the invention is to provide a method of encapsulating perfluorocarbons and other moderately volatile liquids.

Another object of the invention is to provide a method of forming gas-filled lipid vesicles.

A further object of the invention is to provide a whitener which could be used in a variety of industrial applications.

These and other objects and features of the invention will be apparent from the following description.

SUMMARY OF THE INVENTION

In one aspect, the present invention features a method of making paucilamellar lipid vesicles having a moderately volatile liquid encapsulated therein as well as the vesicles themselves. In another aspect, the invention features gas-filled paucilamellar lipid vesicles. These gas-filled vesicles are made by replacing the moderately volatile liquid with a gas so as to leave a gas-filled central cavity. The gas-filled paucilamellar lipid vesicles can be used as whiteners for the paint industry, while the vesicles having the moderately volatile liquid have substantial utility as oxygen carriers.

Paucilamellar lipid vesicles having a moderately volatile liquid encapsulated therein have 2–10 lipid bilayers surrounding the large, amorphous central cavity. The first step in manufacturing these vesicles is forming a lipid phase by blending the wall-forming lipid (which provides the structure to the vesicles) and any other lipid soluble materials which are to be incorporated into the walls. One lipid soluble material which is often used is a sterol such as cholesterol which assists in the thermotropic phase transition. If any oil distinct from the moderately volatile liquid is to be encapsulated into the central cavity, it can be added at this stage or "cold loaded" later. This lipid phase is then hydrated with an excess of an aqueous phase under gentle to moderate shear to form paucilamellar lipid vesicles. If oil is added into the lipid phase, the oil fills at least part of the central core. If no oil is added, the core is filled with the aqueous hydrating solution.

The vessels can then be "cold loaded" with a moderately volatile liquid using the techniques described in U.S. patent application Ser. No. 598,120, now U.S. Pat. No. 5,160,669. Preferably, any oil to be carried by the vesicles is loaded at this stage using the same procedure. Briefly, the formed vesicles are mixed with the moderately volatile liquid under gentle to moderate shear conditions, thereby encapsulating the moderately volatile liquid in the central cavity and driving off some (or all) of the water from the core.

Under certain circumstances, "hot loading" of the vesicles with the moderately volatile liquid is preferred. This is accomplished by dispersing or premixing the moderately volatile liquid in the lipid phase before hydration. This allows the hydration and mixing steps to be carried out simultaneously. However, using the "hot loading" technique, special care must be taken to keep the lipid phase homogeneous during hydration.

If the paucilamellar lipid vesicles having the moderately volatile liquid encapsulated therein are to be used as is, they are merely separated from the reactants. However, if gas-filled, e.g., air-filled, paucilamellar lipid vesicles are being formed, the aqueous solution and the moderately volatile liquid must be removed. This is accomplished by evaporating both liquids, e.g., by air drying, vacuum drying, or lyophilization of the vesicles. Vacuum drying is preferred. The gas-filled paucilamellar lipid vesicles may be used as a whitener because of their refractive properties.

A broad variety of wall-forming lipid materials may be used in the invention. Nonionic lipids, e.g., nonionic surfactants, are preferred. These nonionic lipids are preferably polyethylene fatty acid esters, polyethylene fatty acid ethers, diethanolamides, long chain acyl hexosamides, long chain acyl amino acid amides, long chain amino acid amines, polyoxyethylene sorbitan esters, polyoxy glycerol mono-and diesters, glycerol mono- and distearate, glycerol mono-and dioleate, glycerol mono-and dipalmitate, and mixtures thereof. The most preferred lipids have a melting temperature of about 40° C. or greater. In addition to the nonionic lipids, certain charged lipids such as sarcosinates (sarcosinamides), betaines, and monomeric and dimeric alkyds have been found to be useful. Further, phospholipids such as phosphatidylcholine can be used.

An additional structural support material may be added to further stabilize the vesicles. This additional material is preferably a water soluble polymerizable material that provides additional structural support to the vesicles upon polymerization. Preferred water soluble polymerizable materials are gelatins, acrylates, acrylamides, alginates, carboxymethylcellulose, and similar polymers.

A moderately volatile material useful in the invention must meet the following criteria:

1. It must be less volatile than the aqueous solution in the vesicle.
2. It must be more volatile than the lipid forming the walls of the vesicle.
3. It can be evaporated or volatilized from the lipid vesicle without damaging the structural integrity of the lipid vesicle.
4. It is substantially immiscible with aqueous solutions.
5. It is substantially immiscible with the lipid forming the wall structure.
6. It is substantially unreactive with the lipid forming the wall structure.

These criteria are met by a number of materials such as certain silicones and certain mineral spirits but the perfluorocarbons are preferred. Most preferred perfluorocarbons are perfluorodecalin, perfluorohexane, perfluorooctane, and perfluorodimethylcyclohexane, perfluorotripropylamine, octafluorocyclobutane, and mixtures thereof. Most preferred perfluorocarbons are oxygen carrying molecules such as perfluorodecalin and perfluorotripropylamine.

As noted, an oil can also be incorporated into the central cavity of the vesicle. If an oil is used, it should be immiscible with the lipid forming the bilayers, immiscible with aqueous solutions, and immiscible with said moderately volatile liquid. The oil may act as a carrier for certain oil soluble materials which can be incorporated into the central cavity of the vesicle. Similarly, water soluble materials can be carried in the aqueous phase if they do not form crystals larger than the vesicles upon drying.

DESCRIPTION OF THE INVENTION

The present invention provides methods of making vesicles having gas-filled or moderately volatile liquid filled cores and the vesicles themselves. Vesicles with moderately volatile liquids can be used either on their own, e.g., as oxygen carriers, or as an intermediate in the process of manufacturing the gas-filled vesicles.

Paucilamellar lipid vesicles having aqueous or oil-filled central cavities can be manufactured using standard techniques such as those disclosed in U.S. Pat. No. 4,911,928 or U.S. Pat. No. 4,855,090, the disclosure of which is also incorporated herein by reference. These vesicles are then "cold loaded" with the moderately volatile liquid by mixing the preformed vesicles with the moderately volatile liquid, preferably under gentle to moderate shear conditions. A syringe technique such as is described in U.S. patent application Ser. No. 598,120, now U.S. Pat. No. 5,160,669, is preferred. This technique provides a liquid shear which is approximately equal to a relative flow rate of about 5–50 m/s though a 1 mm radius orifice.

The perfluorocarbons are the preferred moderately volatile liquids but other materials such as certain silicone oils or volatile mineral spirits can also be used. The primary requirements are unreactivity with the lipid wall structure, immiscibility between the moderately volatile liquid and the lipid and aqueous solutions (as well as any oil to be encapsulated) and the ability to be evaporated from the vesicle without damaging the vesicle at a rate slower than the water is evaporated. Evaporation of the aqueous solutions and moderately volatile liquid can be carried out by a variety of methods. However, high heat evaporation should not be used as the lipid structure itself will be melted if too much heat is applied, thereby degrading the vesicles and defeating the purpose of the procedure. Similarly, too high a vacuum cannot be used. While lyophilization is an effective method of removing the liquids, it may be unnecessarily expensive except for large bulk production.

The following Examples will more clearly illustrate the present invention.

EXAMPLE 1

In this Example, a number of different vesicles were made using polyoxyethylene-9 glyceryl monostearate and cholesterol as the wall-forming material. First, a 3:1 ratio of polyoxyethylene-9 glyceryl monostearate and cholesterol was heated to approximately 70° C. (sufficient to obtain free flowing of the reactants) to form a lipid phase. The lipid phase was hydrated with an aqueous phase consisting of phosphate buffered saline at about 65° C. In certain of the experiments, gelatin was added as part of the aqueous phase. Hydration was accompanied by placing approximately 2 ml of the lipid in a 25 ml syringe, approximately 8 ml of the aqueous phase in a second 25 ml syringe, and connecting the two syringes via stopcock with 1 mm diameter orifice. The vesicles were made by syringing the material back and forth through the stopcock for approximately two minutes. This provides the requisite shear for vesicle formation. In fact, a method of providing "shear mixing," as the term is defined in U.S. Pat. No. 4,911,928, would be acceptable.

Approximately 5 ml of the vesicles was blended with 1 ml of the test solution and syringed again for approximately two minutes. The test solution was water (designated "O"), perfluorooctane (a perfluorocarbon) or cyclomethicone (a silicone oil). The vesicles were then separated, observed under a light microscope to insure vesicle formation, placed on a glass slide and desiccated overnight. Table 1 lists the ingredients for each test sample.

TABLE 1

| Sample No. | Gelatin Concentration | Moderately Volatile Liquid |
|---|---|---|
| A | 0 | 0 |
| B | 1% | 0 |
| C | ½% | 0 |
| D | 1% | perfluorooctane |
| E | 1% | cyclomethicone |
| F | ½% | perfluorooctane |
| G | ½% | cyclomethicone |
| H | 0 | cyclomethicone |
| I | 0 | perfluorocarbon |

After desiccation, a drop of oil was placed on each sample and the sample was viewed directly and under a light microscope. Sample A showed a barely noticeable haze under the microscope while samples B and C were gelatin-like. Since none of these samples included a moderately volatile oil, samples A–C provided controls for the plain water, 1% gelatin, and ½% gelatin aqueous phases used in forming the vesicles. However, the perfluorocarbon samples and the cyclomethicone samples all showed some level of opaqueness, indicated light refraction in the central void, of the vesicles. More particularly, sample D was intensely white and granular. Under high power microscopy, all of the opaque samples were shown to consist of packed, highly refractile granules with central voids. Upon rehydration, the granules detached as typical spherical vesicles associated with some gelatin flakes. Sample E, which was identical to sample D, except cyclomethicone replaced the perfluorooctane, was less intensely white than sample D but still showed a white color. Similarly, sample F was intensely white (whiter than sample E) and granular. Upon rehydration, irregular shaped vesicles were apparent. Sample G was white but less intense than sample F. Sample H also showed white granules similar to those of samples E and G while sample I formed an opaque sheet of ovoid spheres. Upon rehydration, vesicles reformed in all the samples made with the moderately volatile liquids.

This Example indicates that there clearly is a void formed in the moderately volatile liquid vesicles after drying. Further, it indicates that a material like a perfluorocarbon is preferred to a cyclomethicone because of the greater white (or refractile) intensity.

EXAMPLE 2

In this Example, a similar test to that described in Example 1 was carried out except the lipid used to form the vesicle was polyoxyethylene-4 stearyl alcohol in lieu of the polyoxyethylene-9 glyceryl monostearate. The vesicles were prepared using 4 ml of the heated lipid solution and 16 ml of an aqueous solution, either with or without gelatin in the aqueous phase. Again, the lipid phase was heated to approximately 70° C., the aqueous phase was heated to approximately 65° C., and the phases were blended using the syringe method described in Example 1. After the vesicles were allowed to cool to room temperature, 5 ml of the vesicles were mixed with water, cyclomethicone (Dow Corning 344) or perfluorooctane in a 5 ml vesicle:1 ml moderately volatile liquid ratio using the previously described syringe technique.

The samples were vacuum dried and allowed to stand for two days in air to insure drying and each sample was observed by light microscopy under oil. Table 2 lists the materials used in forming the various samples.

TABLE 2

| Sample No. | Gelatin Concentration | Moderately Volatile Liquid |
|---|---|---|
| A | 0 | 0 |
| B | 1% | 0 |
| C | ½% | 0 |
| D | 0 | cyclomethicone |
| E | 0 | perfluorooctane |
| F | 1% | cyclomethicone |
| G | 1% | perfluorooctane |
| H | ½% | cyclomethicone |
| I | ½% | perfluorocarbon |

Again, the first three samples (A-C) act as controls for the other samples. Under direct light microscope observation by placing a drop of oil over the dried vesicles, the solution was merely hazy if no moderately volatile liquid was used. Before drying, heterogenous large vesicles had been apparent. These materials did not rehydrate into vesicles.

Sample D also looked hazy under the oil but was somewhat more opaque than the control samples. Upon rehydration, vesicles reformed, showing that the bilayer structure still existed. Similar results were expected from samples F and H but no observation was made upon hydration.

Sample E, containing encapsulated perfluorooctane, showed results similar to those described in Example 1. This sample, when viewed under oil, was white and opaque, showing a network of vesicles. Upon rehydrating, detached vesicles were abundant. Similarly, sample G was also opaque but the vesicles seemed slightly distorted. Upon rehydration, the vesicles were more tightly held than those of sample E, e.g., they did not flow as much. The rehydrated vesicles for sample G appeared to be in the form of sheets of defined vesicles. Sample I gave similar results to sample G.

This Example establishes that the described procedure for vesicle manufacture having a moderately volatile liquid will form vesicles with a central void upon dehydration and that vesicles can be formed upon rehydration.

EXAMPLE 3

In this Example, the same procedures and materials were followed as in Examples 1 and 2 except the lipid used was glycerol monostearate. Similar results were obtained, with an inability to rehydrate vesicles without the moderately volatile liquid, a mild haze to a waxy-like surface observed under oil for the cyclomethicone vesicles, and opaque network of vesicles for the perfluorooctane vesicles. With 1% gelatin added, the hollowness of the perfluorooctane vesicles was clearly evident upon light observation. Again, all of the moderately volatile liquid filled vesicles were rehydratable.

EXAMPLE 4

In this Example, a different lipid, dimethyldistearyl amine (Arosurf) was used as the primary lipid in vessel wall. A lipid phase of 12.21 g of dimethyldistearyl amine was blended with 2.74 g of cholesterol and heated to 100° C. About 2 ml of the heated lipid was then blended with 8 ml of an aqueous solution (either deionized water, 1% gelatin, or ½% gelatin) using the syringe method described in Example 1 to form vesicles. The vesicles were allowed to cool and 5 ml of the vesicles were syringe blended (using the method described in Example 1) with 1 ml of perfluorooctane. The resulting perfluorooctane containing vesicles were dried and observed under oil. All three perfluorooctane preparations showed opaque networks of particles with refractile edges. Upon rehydration, the vesicles were very adhesive and came off in sheets.

EXAMPLE 5

In this Example, a water soluble dye, crystal violet, was added to the hydrating solution in order to determine what was actually happening with the loading technique. About 4 ml of polyoxyethylene-9 glyceryl monostearate was heated to 70° C. and blended with 16 ml of a 0.5% crystal violet solution using the syringe technique described in Example 1. The vesicles were cooled to room temperature and 10 ml of the vesicles were blended, using the syringe technique described in Example 1, with 2 ml of perfluorodecalin. The resulting vesicles were dialyzed overnight in a 3500 molecular weight cut-off dialysis bag against 100 volumes of distilled water. This dialysis step was to remove any crystal violet which had not been encapsulated within the vesicles. After dialysis, the blue color of the vesicles remained, showing incorporation of the crystal violet into the aqueous solution in the vesicles. The vesicles were then dried under vacuum and appeared very granular. The vesicles were lyophilized and rehydrated and the blue color reappeared, showing that while the water from the aqueous solution had been driven out by the drying step, the dye itself was retained in the dried vesicles. Upon redialysis, only a small amount of the dye was released. This method could be used to provide dry storage of the water soluble active materials.

EXAMPLE 6

This Example describes the ability of the vesicles of the invention to carry oil-soluble materials. The particular oil soluble material tested was a dye, oil red O.

First, the vesicles were made by blending 4 ml of polyoxyethylene-9 glyceryl monostearate with 16 ml of deionized water using the syringe technique of Example 1. After separation of the vesicles, and cooling to room temperature, 10 ml of the formed vesicles were blended with 2 ml of a mixture of 0.1% oil red 0 in mineral oil (Drakeol 19). The dye-containing oil and vesicles were syringed by the procedure of Example 1 for approximately two minutes, Providing encapsulation of the oil. About 12 ml of the oil-filled vesicles were then blended with 2 ml of perfluorodecalin using the syringe technique of Example 1. The sample was observed under a light microscope before and after the addition of the perfluorodecalin. After observation, the vesicles were centrifuged for fifteen minutes at 3500 rpm. No separation of dye or perfluorodecalin was observed.

Light microscopy (1000×) showed that before the addition of the perfluorodecalin, the oil substantially filled the central cavity. However, after the addition of perfluorodecalin, the central cavity showed a clear differentiation between the oil and the perfluorodecalin with a substantially flat boundary. This is probably because of the difference in surface tension between the two materials.

After drying, the vesicles were in the form of granules with an oil center. These granules were then lyophilized and rehydrated into vesicles. Only a trace of free oil was released upon rehydration.

The foregoing Examples are purely illustrative and are expressly nonlimiting. Those skilled in the art will recognize other modifications and variations which may be made in the techniques described herein in order to practice the invention. Such other modifications and techniques are within the following claims.

What is claimed is:

1. A paucilamellar lipid vesicle comprising a large, amorphous central cavity surrounded by 2–10 lipid bilayers having a moderately volatile liquid encapsulated in said central cavity, said moderately volatile liquid having the following properties:
   a) it is less volatile than aqueous solutions,
   b) it is more volatile than the lipid and any materials forming said lipid bilayers,
   c) it can be evaporated from said lipid vesicle without damaging the structural integrity of said lipid vesicle,
   d) it is substantially immiscible with aqueous solutions,
   e) it is substantially immiscible with the lipid forming said lipid bilayers, and
   f) it is substantial unreactive with the lipid in said lipid bilayer.

2. The paucilamellar lipid vesicle of claim 1 wherein said moderately volatile liquid comprises a perfluorocarbon.

3. An oxygen carrier comprising the perfluorocarbon filled vesicle of claim 2.

4. The paucilamellar vesicle of claim 2 wherein said perfluorocarbon is selected from the group consisting of perfluorodecalin, perfluorohexane, perfluorooctane, perfluorodimethylcyclohexane, perfluorotripropylamine, octafluorocyclobutane, and mixtures thereof.

5. The paucilamellar lipid vesicle of claim 4 wherein said perfluorocarbon comprises a perfluorocarbon capable of carrying oxygen.

6. The paucilamellar lipid vesicle of claim 1 further comprising an oil, said oil being immiscible with said lipid, immiscible with said aqueous solutions and immiscible with said moderately volatile liquid.

7. The paucilamellar lipid vesicle of claim 6 wherein said oil has oil-soluble materials carried therein.

8. The paucilamellar lipid vesicle of claim 1 wherein said lipid comprises a lipid with a melting temperature of at least about 40° C.

9. The paucilamellar lipid vesicle of claim 8 wherein said lipid comprises a nonionic lipid.

10. The paucilamellar lipid vesicle of claim 1 wherein said lipid comprises a phospholipid.

11. A method of manufacturing gas-filled paucilamellar lipid vesicles having 2–10 lipid bilayers surrounding a substantially amorphous, gas-filled central cavity comprising the steps of:
    a) hydrating the lipid to be used as the primary structural wall material with an aqueous solution to form paucilamellar lipid vesicles filled with said aqueous solution in said central cavity,
    b) mixing said lipid vesicles with a moderately volatile liquid that is (1) substantially immiscible with said lipid, (2) substantially immiscible with aqueous solutions, (3) less volatile than aqueous solutions, (4) more volatile than said lipid, (5) substantially unreactive with lipid, and (6) can be evaporated from said lipid without damaging the structural integrity of said paucilamellar lipid vesicles to form moderately volatile liquid filled paucilamellar lipid vesicles,
    c) removing said aqueous solution and said moderately volatile material from said paucilamellar lipid vesicles without damaging the structural integrity of said paucilamellar lipid vesicles,
    whereby said gas-filled paucilamellar vesicles are formed.

12. The method of claim 11 wherein said removing step comprises air drying.

13. The method of claim 11 wherein said removing step comprises vacuum drying.

14. The method of claim 11 wherein said removing step comprises lyophilizing.

15. The method of claim 11 wherein said moderately volatile liquid comprises a perfluorocarbon.

16. The method of claim 15 wherein said perfluorocarbon is selected from the group consisting of perfluorodecalin, perfluorohexane, perfluorooctane, perfluorodimethylcyclohexane, perfluorotripropylamine, octafluorocyclobutane, and mixtures thereof.

17. The method of claim 11 wherein said lipid comprises a lipid with a melting temperature of at least about 40° C.

18. The method of claim 11 wherein said mixing step further comprises mixing oil that is immiscible with said lipid and immiscible in said moderately volatile liquid.

19. The method of claim 11 comprising the step of dispersing said moderately volatile liquid in said lipid before hydration, thereby simultaneously carrying out said steps of hydrating said lipid and mixing said lipid vesicles with said moderately volatile liquid.

* * * * *